United States Patent [19]
Hahn

[11] Patent Number: 6,083,933
[45] Date of Patent: Jul. 4, 2000

[54] TREATMENT OF CYSTITIS-LIKE SYMPTOMS WITH CHONDROITIN SULFATE FOLLOWING ADMINISTRATION OF A CHALLENGE SOLUTION

[75] Inventor: Sungtack Samuel Hahn, Scarborough, Canada

[73] Assignee: Stellar International Inc., London, Canada

[21] Appl. No.: 09/294,019

[22] Filed: Apr. 19, 1999

[51] Int. Cl.[7] ........................ A61K 31/715; A61K 31/725
[52] U.S. Cl. ................................ 514/54; 514/56; 536/21; 536/118; 424/9.2
[58] Field of Search .................... 514/54, 56; 424/9.2; 536/21, 118

[56] References Cited

U.S. PATENT DOCUMENTS

| | | | |
|---|---|---|---|
| 5,753,266 | 5/1998 | Youssefyeh et al. | 424/484 |
| 5,880,108 | 3/1999 | Morales et al. | 514/54 |

FOREIGN PATENT DOCUMENTS

| | | |
|---|---|---|
| 1187798 | 5/1985 | Canada . |
| 1240929 | 8/1988 | Canada . |
| 1258452 | 8/1989 | Canada . |
| 1277239 | 12/1990 | Canada . |
| 2071898 | 4/1991 | Canada . |
| 2075930 | 8/1991 | Canada . |
| 2020199 | 12/1991 | Canada . |
| 2046037 | 1/1992 | Canada . |
| 1305134 | 7/1992 | Canada . |
| 2060223 | 8/1992 | Canada . |
| 1307525 | 9/1992 | Canada . |
| 2042152 | 11/1992 | Canada . |
| 2066785 | 11/1992 | Canada . |
| 2110291 | 12/1992 | Canada . |
| 2076063 | 2/1993 | Canada . |
| 1315683 | 4/1993 | Canada . |
| 1316828 | 4/1993 | Canada . |
| 2100657 | 5/1993 | Canada . |
| 2120367 | 1/1994 | Canada . |
| 2100197 | 2/1994 | Canada . |
| 2159591 | 10/1994 | Canada . |
| 2128160 | 1/1995 | Canada . |
| 2130295 | 2/1995 | Canada . |
| 2190107 | 11/1995 | Canada . |
| 2218872 | 10/1996 | Canada . |
| 2232527 | 3/1997 | Canada . |
| 2203621 | 4/1998 | Canada . |
| 2217134 | 4/1998 | Canada . |
| 9400135 | 1/1994 | WIPO . |

OTHER PUBLICATIONS

Hurst et al, J. Urol., 138:433–437, 1987: (Aug., 1987). "Functional and Structural Characteristics of the Glycosaminoglycans of the Bladder Luminal Lining".

Conte et al, Arzneim–Forsch./Drug Res. 41(II), 7, 768–772 (1991) "Metabolic Fate of Exogenous Chondroitin Sulfate in Man".

Sant & LaRock, "Standard Intravesical Therapies for Interstitial Cystitis", in Urologic Clinics of North America, vol. 21, No. 1, Feb. 1994, at pp. 73–83.

Hurst et al, Urology 48:817–821, 1996 "A Deficit of Chondroitin Sulfate Proteoglycans on the Bladder Uroepithelium in Interstitial Cystitis".

Parsons et al, J. Urol., 159:1862–1867, 1998 (Jun., 1998). "The Role of Urinary Potassium in the Pathogenesis and Diagnosis of Interstitial Cystitis".

Schick, Canadian Journal of CME, Aug. 1998, pp. 55–66 "Interstitial Cystitis: Diagnosis and Treatment".

Internet Web Site www.ichelp.com accessed Jan. 15, 1999, Mast cells may account for success of GAG layer treatments, by editor Norman Bauman.

Erickson et al., "Urinary Chondroitin Sulfates, Heparin Sulfate and Total Sulfated Glycosaminoglycans in Interstitial Cystitis," *Journal of Urology,* 157(1), 61–64 (Jan., 1997).

Berkow et al. (eds.), *Merck Manual of Diagnosis and Therapy,* 16th Edition, Merck & Co., Rahway, NJ, 1992, only title & text pp. 1713–1714, 1722 and 2082 supplied.

*Primary Examiner*—Gary Geist
*Assistant Examiner*—L. E. Crane
*Attorney, Agent, or Firm*—James E. Gastle

[57] ABSTRACT

Cystitis of the bladder and urinary tract, particularly interstitial cystitis, are treated using effective unit doses of chondroitin sulfate. Further, cystitis patients are screened for their response to a given cystitis treatment using a method in which patients are first challenged with an irritant and then treated with a selected cystitis therapeutic. Candidates for further treatment are identified as those patients who on receiving the selected therapeutic, report relief from at least one symptom elicited with the irritant. Also provided are kits comprising solutions for carrying out this screening method.

23 Claims, No Drawings

6,083,933

TREATMENT OF CYSTITIS-LIKE SYMPTOMS WITH CHONDROITIN SULFATE FOLLOWING ADMINISTRATION OF A CHALLENGE SOLUTION

FIELD OF THE INVENTION

The invention relates to therapeutic and diagnostic methods useful in the treatment and assessment of cystitis, including interstitial cystitis, and related bladder conditions.

BACKGROUND TO THE INVENTION

Interstitial cystitis is a bladder condition associated with discomfort and pain elicited by urinary irritants, causing urgency for, and increased frequency of, urination. Because its cause is poorly understood, the development of useful treatments has followed approaches that are largely empirical and even haphazard, and these approaches have failed to yield more than a few useful therapeutic agents and treatments. As described by Sant and La Rock in Interstitial Cystitis, Vol. 21 (1), February 1994 at p.73, current therapies include pharmacotherapy, with intravesical use of dimethyl sulfoxide being the only therapy approved by the FDA. Still, a variety of other agents are in use to treat symptoms of interstitial cystitis, either alone or in combination with DMSO. Such agents include sodium oxychlorosene (Clorpactin), heparin, hyaluronic acid, steroid, sodium bicarbonate, silver nitrate, sodium pentosanpolysulfate, cromolyn sodium, lidocaine and doxorubicin. Many of these agents can be delivered orally, but to be effective are most typically delivered by instillation either as monotherapy, combination therapy or sequential therapy. These agents and therapies target the bladder mucosal lining, and provide symptomatic relief of pain, frequency and urgency. Of these therapies, however, few offer relief over sustained periods.

There is a need to provide, on a cost-effective basis, agents and therapies that are useful to treat cystitis, including interstitial cystitis and related conditions of the bladder and urinary tract that result from an eroded mucosal lining. There is also a need to provide methods by which patients can be screened to reveal therapeutic agents effective to treat that patient's particular condition. It is accordingly an object of the present invention to provide such a diagnostic screening method.

SUMMARY OF THE INVENTION

For use in treating various forms of cystitis as they affect the bladder and urinary tract, particularly including interstitial cystitis, the present invention exploits chondroitin sulfate in effective unit doses. Effective unit doses particularly are those which provide relief from at least one symptom elicited in a patient upon instillation of an irritant.

Thus, in accordance with one aspect of the invention,there is provided a method for treating a patient afflicted with interstitial cystitis or related condition of the the bladder or urinary tract, the method comprising the step of delivering to the patient by instillation a pharmaceutical composition comprising a dose of chondroitin sulfate effective to alleviate at least one symptom elicited in such a patient by instillation of an irritant.

In other aspects of the invention, there are provided pharmaceutical compositions adapted for delivery to a patient by instillation,the compositions comprising an amount of chondroitin sulfate effective to alleviate at least one of the symptoms that elicited in a cystitis patient upon instillation of an irritant. In embodiments of the invention, compositions effective to treat cystitis include sterile, aqueous compositions comprising:

(1) a unit dose of injectable grade chondroitin sulfate of up to about 200 mgs, e.g., in the range from 40 mgs to 120 mgs, and (2) a pharmaceutically acceptable aqueous carrier, in a volume that is patient-tolerated and sufficient for exposing the bladder surface area to be treated.

Also provided by the present invention is a method useful for screening patients to identify patients likely to respond to a given cystitis therapy, the method comprising the steps of (1) delivering to the patient by instillation a challenge solution containing an irritant effective to elicit symptoms in a patient afflicted with cystitis, (2) draining the irritant solution after the symptoms are elicited, and then (3) delivering to the patient by instillation a neutralizing solution comprising an agent having interstitial cystitis treatment properties, whereby patient responders are identified as those patients reporting relief from at least one symptom elicited by the challenge solution, when the neutralizing solution is instilled.

This diagnostic screening method of the invention can usefully be applied to any agent whose utility in treating IC is known or is under investigation.

Also provided by the present invention is a kit useful clinically for performing the method just described, the kit comprising, in combination, (1) a first sterile neutralizing solution comprising an effective amount of an agent, such as chondroitin sulfate, useful to treat symptoms of interstitial cystitis or related bladder condition, and an aqueous vehicle, (2) a second sterile challenge solution comprising an irritant for eliciting a response in a patient afflicted with cystitis or having an eroded bladder lining; and (3) printed instructions teaching the use, in combination, of the first and second sterile solutions in accordance with the method just described.

Other aspects of the invention and embodiments thereof are now described in greater detail hereinafter.

DETAILED DESCRIPTION AND PREFERRED EMBODIMENTS

The compositions and methods of the present invention are useful in the treatment and assessment of various forms of cystitis as they occur particularly in the bladder, but also as they occur in the urinary tract including the urethra and those other mucosal surfaces that are exposed to treatment by the vesicular instillation route of administration. By this route, a sterile catheter is placed into the bladder through the urethra, and the treatment solution fed through the catheter. Solution drainage is similarly through the catheter, by gravity flow. The forms of cystitis that can be treated include particularly interstitial cystitis and those other forms of cystitis and related bladder conditions that respond to an enhancement of mucosal integrity and barrier function that is believed to result when the present chondroitin sulfate treatment is used. These include radiation-induced cystitis and hemorrhagic cystitis.

For use in treating interstitial cystitis and these related conditions, the present invention exploits chondroitin sulfate which is an acidic mucopolysaccharide and is one of the glycosaminoglycans (GAGs). Its repeating disaccharide unit is made of glucuronic acid and galactosamine with one sulfate group in a B (1-3') linkage, i.e. N-acetyl galactosamine sulfate. This disaccharide unit is polymerized in B (1-4') linkage.

Chondroitin sulfate (CS) is available in a number of mono-sulfated forms, varying according to specific chemical composition usually as related to extraction source, chain length usually as related to processing techniques, degree of sulfation, etc. For use in the present invention, the CS is desirably in pyrogen free form and is highly purified, thus yielding an "injectable grade" of material having the qualities required for human use by the various regulating agencies. Such material is available from a variety of commercial sources, and the present literature is replete with descriptions of methods suitable for producing such material. In embodiments of the invention, the CS is within the molecular size range of from about 5,000 Daltons to about 75,000 Daltons, for example from about 10,000 Daltons to about 40,000 Daltons. A suitable natural source for CS within this size range is soft connective tissue, such as cartilage. In a specific embodiment, the CS starting material is obtained from bovine cartilage and subsequently refined by established methods to yield the desired injectable grade and molecular size fractionated CS. Alternatively, it will be appreciated that the CS can be obtained from other sources, including synthetic routes, or can be blended to combine synthetic and natural CS forms into the desired composition. Desirably, but not essentially, the CS comprises the A-form and C-form of CS, in a blend of form 3:1 to 1:3 on a molar basis, e.g., about 1:1.

It will be understood that the CS typically is in salt form, and in accordance with embodiments of the invention, is in the sodium salt form.

For use, the CS is formulated as a sterile, aqueous solution. The formulation is desirably adapted for single dose administration, although it will be appreciated that a multi-dose formulation may be utilized to treat a number of patients. The unit dose of CS suitable for administration to the patient may vary depending on the severity of the condition, the type of ailment whether interstitial cystitis or related condition, and the duration of treatment. A useful unit dose for an adult afflicted with interstitial cystitis can be 200 mgs or higher, but more typically will be within the range from 40 mgs to 120 mgs, preferably from 60 mgs to 100 mgs and more preferably from 70 mgs to 90 mgs. In a specific embodiment of the invention, the unit dose is about 80 mgs.

The unit dose of CS is desirably formulated in a solution volume sufficient to expose the bladder surface to be treated, and is at least tolerable and more desirably comfortable for the patient. The upper limit for such volumes lies below the volume causing hydrodistention. For adult patients, solution volumes are suitably up to about 100 mL, e.g. up to about 75 mL, and preferably up to about 50 mL. In a specific embodiment of the invention, a solution volume of about 40 mL is utilized.

As vehicle for such solutions, there may be employed sterile water, saline or buffered saline. The saline vehicle is particularly useful, and in embodiments of the invention, the vehicle is 0.9% saline. Alternatively, phosphate buffered saline vehicles may be used.

The concentration of CS within the solution will of course vary in accordance with the amount of CS formulated and the solution volume employed. CS is relatively soluble in aqueous vehicles, and a wide range of concentrations may therefore be formulated. In embodiments of the invention, the CS concentration lies within the range from 0.1 mg/mL to 100 mg/mL, preferably 1.0 mg/mL to 20 mg/mL. In a specific embodiment of the invention, the formulation has a CS concentration of about 2 mg/mL. In a particular specific embodiment of the invention, the formulation achieves this concentration by providing a formulation containing 80 mgs of CS in a 40 mL volume of phosphate buffered saline. In another embodiment of the invention, the CS is formulated at high concentration, containing about 80 mgs of CS in 4 mL of vehicle. Such a composition is suitable particularly as a concentrate, for use in "spiking" a standard 2 mg/mL solution to increase the CS dose made available to the patient upon instillation where desired.

Formulation of the CS will of course be performed in a manner established in the pharmaceutical art. Unit or single doses can be produced simply by metering the unit dose of CS, say 80 mgs, into a vial which then receives 40 mL of vehicle or diluent, under aseptic filling conditions.

In use, the CS composition is administered by instillation or like method that directs the composition to the luminal (mucosal) surface of the affected bladder or associated surface of a patient having the symptoms of cystitis including radiation-induced cystitis, hemorrhagic cystitis and, in accordance with a preferred embodiment of the invention, interstitial cystitis. In addition to IC patients, such treatment can be useful, as noted, for "related bladder conditions", i.e., for those patients having an erosion of either the bladder lining or the lining of the urethra or ureters which is sufficiently severe to cause pain or discomfort when chemical irritants are present in the urine. With each treatment, the composition is instilled, for instance as a 2.0 mg/mL dose of CS in a buffer volume of 40 mL, after any residual urine has been removed. The patient then retains the solution for a period desirably of not less than 30 minutes. In a typical treatment regimen, weekly treatments are performed for about 4 weeks, and then monthly treatments are performed thereafter until symptoms are relieved. Some patients may benefit from up to 6 weekly instillations, then instillations once monthly thereafter depending on their symptomatic response.

As noted in the examples, patients treated in the manner just described have responded well, by indicating that symptoms of pain, urgency and/or frequency have subsided. Particularly, in human clinical studies, it has been revealed that 5 of 6 subjects have remained asymptomatic for periods longer than 8 months, indicating that the treatment with CS does not have the drawback of regression seen with other therapies.

The present success with chondroitin sulfate is both a surprising and significant result, given, on the one hand, that chondroitin sulfate is both a commercially available and relatively inexpensive agent and, on the other hand, that so few agents tested for IC are found to provide actual benefit to the patient. Because diagnosis of IC is difficult, and because identification of useful therapeutic agents has been so elusive, there is provided in another aspect of the invention a method by patients are screened to identify responders to a given IC therapy. Particularly, the present invention further provides a method comprising the steps of:

delivering to the bladder of a given patient, a challenge solution containing an irritant in an amount and for a period of time sufficient to elicit a symptom in a patient having an eroded bladder epithelium;

draining the challenge solution after the sensation is elicited; and then instilling a neutralizing solution containing a selected agent useful to treat cystitis, whereby patients reporting relief from the challenge solution are identified as candidates for subsequent treatment with the selected cystitis treatment agent.

It will thus be appreciated that the present method is capable not only of indicating that a given patients suffers from interstitial cystitis or a condition related by an erosion of the bladder lining but, significantly, also of revealing those patients who would benefit from treatment with a particular cystitis treatment agent. This approach has the advantage of identifying therapies that are adapted particularly for use in treating a given patient and the particular form or severity of cystitis presented by that particular patient.

For use in this method, the eliciting of a sensation in a given patient can be achieved using various irritants. In a specific embodiment of the invention, the irritant is potassium chloride, delivered in a 3.0% sterile solution. Other irritants, such as urea, can also be employed to "challenge" the patient. In general terms, the irritant is any physiologically tolerable agent that will elicit a sensation of discomfort or irritation in a patient having an eroded bladder lining, when delivered to the bladder of such a patient. As with the chondroitin sulfate treatment, the irritant is desirably admninistered by instillation, using a volume of preferably about 40 mL of an aqueous vehicle such as sterile water, saline or PBS. Suitable irritants generally will raise a response in the patient within minutes. In the case of the 3.0% KCl solution for instance, patients typically will respond with a sensation of discomfort within about 2–3 minutes.

For those patients in whom a symptom is elicited by the irritant, the irritant is then drained and the patient is then treated by instillation with a solution containing a selected cystitis treatment agent. As noted, desired cystitis treatment agents are those which "neutralize", i.e., relieve, the sensation elicited by the challenge solution containing the irritant.

The chosen cystitis treatment agent can be any of the currently used agents, or an agent candidate suspected of being useful to relieve the sensation, and hence treat the symptoms of the interstitial cystitis or related condition. Such known agents include those delivered by instillation, such as DMSO, heparin, pentosanpolysulfate and hyaluronic acid. As candidate agents, these may include various agents known to be among the constituents of the bladder lining, including the glycosaminoglycans (GAGs) such as the various forms of hyaluronic acid, other forms of chondroitin sulfate and other forms of heparin. As noted hereinabove, such agents should be administered in a volume sufficient to bathe the bladder lining with an amount of the agent determined to be suitable for investigating a therapeutic effect.

Patients that respond to the agent desirably are continued on therapy with that agent. It is recommended that such therapy continue as once weekly treatments for an additional three weeks, followed by once monthly treatments for about five months or until symptoms have resolved.

For use in this diagnostic method of the present invention, there is further provided by the present invention a kit comprising, in combination, (1) a first sterile solution comprising an amount of chondroitin sulfate sufficient to treat symptoms of interstitial cystitis or related bladder condition and an aqueous vehicle, (2) a second sterile solution comprising an irritant salt for eliciting a response in a patient having an eroded bladder lining; and (3) printed instructions teaching the use, in combination, of the first and second sterile solutions in accordance with the method just described.

Such a kit may take the form of a box or other package in which the first and second sterile solutions are provided in separate vials containing ready-to-use solutions, having the concentrations and unit doses described above. The printed instructions will convey to the end-user the methodology described hereinabove, and as described below in the examples.

EXAMPLES

The following describes the treatment of interstitial cystitis patients in a clinical setting.

For use in treatment, chondroitin sulfate, as the sodium salt, was purchased as injectable grade, non-pyrogenic and highly purified from Bioiberica, S. A. in Barcelona, Spain. The CS was obtained from bovine cartilage to control its purity and composition of chondroitin sulfate in terms of its isomers A/C (60:40) and carboxyl/O-sulfate ratio (about 0.95), with other specifications being the following:

Appearance: white to slightly off-white highly hygroscopic solid powder
Purity (anhydrous basis):>98.0%
pH in 1% water: 5.5–7.5
Specific rotation (4% water): −20 to −30 degrees
Nitrogen (anhydrous basis): 2.5–3.5%
Sulfur (anhydrous basis): 5.0–7.0%
Sulfate ash (anhydrous basis): 21–29%
Heavy metals:<20 ppm
Chloride:<0.1%
Proteins (anhydrous basis):<1.0%
Pyrogen: pyrogen free
Average Molecular Weight: 10,000–40,000 Daltons This CS was formulated as a 2.0 mg/mL solution, by blending, the following ingredients:

| Ingredient | Formula Quantity (per mL) |
| --- | --- |
| Na Chondroitin Sulfate (as anhydrous) | 2.0 mg |
| Sod. Chloride, USP | 8.5 mg |
| Dibasic Sodium Phosphate 7H$_2$O, USP | 0.42 mg |
| Monobasic Sodium Phosphate 2H$_2$O, USP | 0.04 mg |
| Sterile Water for Injection., USP OR Sterile Water for Irrigation USP QS to Volume | |

Sterile Water for Injection., USP
OR
Sterile Water for Irrigation USP QS to Volume For compounding, 40 mL of water for injection, USP, is collected, and the required amount of Sodium Chloride is added and mixed until completely dissolved (a minimum of 15 minutes). The required amount of monobasic and dibasic Sodium Phosphate is then added and mixed until completely dissolved (a minimum of 15 minutes). Then, the required amount of Sodium Chondroitin Sulfate, is added and mixed until completely dissolved (a minimum of 4 hours for hydration). If necessary the pH is adjusted to 7.2 0.1 with IN Sodium Hydroxide in WFI, USP or 1 N Phosphoric Acid in WFI, USP. Then, add sufficient quantity to final volume with sterile water for injection, USP and mix thoroughly.

The compounded solution is then sterile filled as 40 mL aliquots into into 50 mL, molded Flint I type vials previously sterilized at 250 C. for 180 minutes, and stoppered using 100% synthetic rubber stoppers of the 20 mm type. The vials were then labeled as sterile sodium chondroitin sulfate solution, 2.0%, bearing the trademark "Uracyst-S".

For use in the method of the present invention, a 3.0% KCL solution was prepared, using the general processing conditions and vials as described above, as a 30 mg/mL KCl solution buffered to pH 7.0±0.5 in 40 mL of sterile water for injection or irrigation, and labeled "Solution K".

The CS so formulated (40 mL of 0.2%w/v sterile sodium chondroitin sulfate solution, hereinafter termed Uracyst-S) was assessed, with the KCl solution prepared as described above, in a pilot study with six patients diagnosed with interstitial cystitis. More particularly, the pilot study was conducted to assess relief of interstitial cystitis symptoms on potassium sensitive bladders.

Patients with urinary urgency and/or bladder pain were selected randomly as they were referred to the clinic. They were examined to determine that there was no obvious cause for their symptoms such as a bladder infection, urethral stricture, cystitis cystica etc. If the findings were negative the patient was included in this study. Patients were first instilled intravesically with sterile water through a sterile catheter to verify the baseline symptoms of urinary urgency and bladder was, when the bladder was filled. Then, excess water was drained through the installation catheter, followed by instillation of the potassium test solution (Solution K—40 mL Sterile Potassium Chloride Solution, 3.0%). Urgency and pain evoked by the potassium test solution were measured by scoring against the baseline symptoms of the water instillation. Residual potassium solution was drained and Uracyst-S was instilled to measure its effect in neutralizing the potassium evoked symptoms. Those patients responding positive to Uracyst-S neutralization effect, received three further weekly instillations of Uracyst-S, followed by monthly instillation for relief of their interstitial cystitis symptoms.

Six patients reporting a positive instilse to the potassium test were given a bladder instillation of 40 mL of Uracyst-S to neutralize the potassium-evoked symptoms. All six patients reported improvement to their potassium-evoked symptoms ranging from complete to moderate relief. This instillation was considered their first treatment. A further three weekly instillations were administered, then monthly thereafter. These patients are now at month eight. As noted below, five of the six patients showed significant improvement in their baseline symptoms, the sixth patient had some decrease in frequency and nocturia but no significant relief of pain.

In the pilot study, patients with urinary urgency and/or bladder pain were selected randomly as they were referred to the clinic. They were examined to determine that there was no obvious cause for their symptoms such as a bladder infection, urethral stricture, cystitis cystica etc. If the findings were negative, the patient was included in this study. Patients were first instilled intravesically with sterile water to verify the baseline symptoms of urinary urgency and bladder pain, when the bladder was filled. Then, excess water was drained through the instillation catheter, followed by instillation of the potassium test solution (Solution K—Sterile Potassium Chloride Solution 3.0%). Urgency and pain evoked by the potassium test solution were measured by scoring against the baseline symptoms of the water instillation. Residual potassium solution was drained and Uracyst-S was instilled to measure its effect in neutralizing the potassium-evoked symptoms. Those patients responding positive to Uracyst-S neutralization effect, received three further weekly instillations of Uracyst-S, followed by monthly instillation for relief of their interstitial cystitis symptoms.

Six patients reporting a positive response to the potassium test were given a bladder instillation of 40 mL of Uracyst-S to neutralize the potassium-evoked symptoms. All six patients reported improvement to their potassium-evoked symptoms ranging from complete to moderate relief. This instillation was considered their first treatment. A further three weekly instillations were administered, then monthly thereafter. These patients are now at month eight. Five of the six patients showed significant improvement in their baseline symptoms, the sixth patient had some decrease in frequency and nocturia but no significant relief of pain.

Patient #1—HB

Patient has a need to urinate hourly and complains of bladder pain. The response to the potassium test was quite severe for pain and moderate for urgency. Uracyst-S provided total relief of the potassium induced pain symptoms and a mild relief to induced urgency and felt it provided a slight improvement in baseline symptoms. Patient had improvement in frequency but little to no improvement of pain symptoms with continued Uracyst-S instillations (three additional weekly instillations then monthly thereafter).

Patient #2—MM

Complained of frequency and pain even when bladder empties. Cystoscopy and urinalysis were negative. The response to the potassium test was moderately severe for pain and mild to moderate for urgency. Uracyst-S provided total relief of the potassium-induced pain, mild relief of urgency and no improvement in baseline symptoms. Patient's symptoms continue to be well controlled with continued Uracyst-S instillations (three additional weekly instillations then monthly thereafter).

Patient #3—MD

Patient complained of chronic bladder irritation. The response to the potassium test was moderately severe for pain and mildly moderate to urgency. The Uracyst-S provided moderate to total relief of potassium induced pain and urgency, with no improvement in baseline symptoms. This patient continues to respond positively to continued Uracyst-S instillations (three additional weekly instillations then monthly thereafter).

Patient #4—BK

Patient has had moderately severe frequency for the past 3 years and bladder pain that fluctuates from mild to moderate to occasional flares of severe pain. The response to the potassium test was mildly moderate for pain and moderately severe for urgency. Uracyst-S provided mild relief of pain and total relief of urgency induced by the potassium test. There was no improvement in baseline symptoms. This patient's response to continued Uracyst-S was excellent with a total remission of all symptoms.

Patient #5—Mary D

Every two or three weeks patient experienced difficulty with frequency and bladder pain. The response to the potassium test was moderately severe for pain and severe for frequency. The Uracyst-S provided total relief of the potassium induced symptoms with no effect on baseline symptoms. The patient continues to respond to Uracyst-S instillations (three additional weekly instillations then monthly thereafter).

Patient #6—SM

Patient experienced frequency that ranged from moderate to severe and had limited responds to earlier DMSO treatments. The response to the potassium test was moderately severe for urgency with no effect on pain. Uracyst-S provided total relief of the potassium induced urgency. The patient continues to respond positively to Uracyst-S instillations (three additional weekly instillations then monthly thereafter).

We claim:

1. A method for treating a patient afflicted with a bladder or urinary tract condition selected from cystitis and a related condition for which one or more cystitis symptoms are elicited in the afflicted patient upon instillation of a potassium chloride solution, comprising the step of delivering to the patient by instillation a composition comprising a carrier, and an amount of chondroitin sulfate effective to alleviate at least one of the symptoms of said condition.

2. A method according to claim 1, wherein said composition comprises chondroitin sulfate at a dose in the range from 40 mgs to 120 mgs.

3. A method according to claim 1, wherein the chondroitin sulfate is present in the composition at a concentration within the range from 0.1 mg/mL to 100 mg/mL.

4. A method according to claim 3, wherein the chondroitin sulfate is present in the composition at a concentration within the range from 1 mg/mL to 10 mg/mL.

5. A method according to claim 1, wherein the patient is afflicted with interstitial cystitis.

6. A method useful for screening patients to identify responders to a given cystitis therapy, the method comprising the steps of:

(1) delivering to the patient by instillation a challenge solution containing an irritant effective to elicit a response in a patient afflicted with cystitis, (2) draining the irritant solution after the response is elicited, and then (3) delivering to the patient by instillation a neutralizing solution comprising an agent having interstitial cystitis treatment properties, whereby patient responders are identified as those patients reporting relief, from at least one symptom raised by the challenge solution, when the neutralizing solution is instilled.

7. The method according to claim 6, wherein the agent in the neutralizing solution is a glycosaminoglycan.

8. The method according to claim 7, wherein the agent is chondroitin sulfate.

9. The method according to claim 7, wherein the irritant in the challenge solution is potassium chloride.

10. The method according to claim 9, wherein the challenge solution is a 3.0% KCl solution.

11. A kit useful clinically for performing the method of claim 6, the kit comprising, in combination, (1) a neutralizing solution comprising an effective amount of an agent useful to treat symptoms of interstitial cystitis or related bladder condition in which interstitial cystitis symptoms are elicited upon instillation of a 3% KCl solution to an afflicted patient, and an aqueous vehicle, (2) a challenge solution comprising an irritant for eliciting symptoms in a patient afflicted with interstitial cystitis; and (3) printed instructions teaching the use, in combination, of the neutralizing and challenge solutions in accordance with the method of claim 6.

12. A kit according to claim 11, wherein said agent is chondroitin sulfate.

13. A kit according to claim 12, wherein said irritant is potassium chloride.

14. A method for treating a patient afflicted with a bladder or urinary tract condition selected from cystitis and a related condition in which one or more cystitis symptoms are elicited in the afflicted patient by instillation of a potassium chloride solution, the method comprising the step of delivering to the patient by instillation a composition consisting of a pharmaceutically acceptable carrier, and an amount of chondroitin sulfate effective to alleviate at least one of the symptoms of said condition.

15. A method for treating a patient afflicted with a bladder or urinary tract condition according to claim 14, wherein the condition is cystitis.

16. The method for treating a patient afflicted with a bladder or urinary tract condition according to claim 15, wherein the condition is interstitial cystitis.

17. The method for treating a patient afflicted with a bladder or urinary tract condition according to claim 15, wherein the composition delivered by instillation to said patient is a sterile solution consisting of an aqueous vehicle and chondroitin sulfate.

18. The method for treating a patient afflicted with a bladder or urinary tract condition according to claim 17, wherein said chondroitin sulfate is present in said composition at a concentration of from 0.1 mg/ml to about 100 mg/ml.

19. The method for treating a patient afflicted with a bladder or urinary tract condition according to claim 17, wherein said chondroitin sulfate is present in said composition at a concentration of from 1 mg/ml to 20 mg/ml.

20. The method for treating a patient afflicted with a bladder or urinary tract condition according to claim 19, wherein the volume of said composition delivered by instillation to the patient is not more than 100 ml.

21. The method for treating a patient afflicted with a bladder or urinary tract condition according to claim 20, wherein the amount of chondroitin sulfate present in said composition is from 40 mgs to 200 mgs.

22. The method for treating a patient afflicted with a bladder or urinary tract condition according to claim 21, wherein the condition is interstitial cystitis.

23. The method for treating a patient afflicted with a bladder or urinary tract condition according to claim 22, wherein the composition is a sterile solution consisting of up to 100 ml of an aqueous vehicle and from 40 mgs to 120 mgs of chondroitin sulfate.

* * * * *